(12) United States Patent
Schmidt et al.

(10) Patent No.: US 12,090,241 B2
(45) Date of Patent: ***Sep. 17, 2024

(54) DEVICES, SYSTEMS AND METHODS FOR OZONE SANITIZATION OF CONTINUOUS POSITIVE AIRWAY PRESSURE DEVICES

(71) Applicant: SoClean, Inc., Peterborough, NH (US)

(72) Inventors: Michael U. Schmidt, Franklin, MA (US); Timothy Leyva, Bellingham, MA (US); Mariusz Surowaniec, Thompson, CT (US)

(73) Assignee: SOCLEAN INC., Peterborough, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,683

(22) Filed: Mar. 20, 2023

(65) Prior Publication Data

US 2024/0058493 A1 Feb. 22, 2024

Related U.S. Application Data

(63) Continuation of application No. 17/384,314, filed on Jul. 23, 2021, now Pat. No. 11,607,471, which is a continuation of application No. 15/880,962, filed on Jan. 26, 2018, now Pat. No. 11,135,327, which is a continuation of application No. 15/330,789, filed as (Continued)

(51) Int. Cl.
| | |
|---|---|
| *A61L 2/20* | (2006.01) |
| *A61L 2/00* | (2006.01) |
| *A61L 9/00* | (2006.01) |
| *A61L 9/015* | (2006.01) |
| *A61M 16/00* | (2006.01) |
| *A61M 16/06* | (2006.01) |

(Continued)

(52) U.S. Cl.
CPC .............. *A61L 2/202* (2013.01); *A61L 2/00* (2013.01); *A61L 2/0094* (2013.01); *A61L 9/00* (2013.01); *A61L 9/015* (2013.01); *A61M 16/0057* (2013.01); *A61M 16/021* (2017.08); *A61M 16/06* (2013.01); *A61M 16/0875* (2013.01); *A61M 16/16* (2013.01); *A61L 2202/15* (2013.01); *A61L 2202/24* (2013.01); *A61L 2209/212* (2013.01); *A61L 2209/10* (2013.01)

(58) Field of Classification Search
CPC ....................................................... A61L 2/202
See application file for complete search history.

(56) References Cited

U.S. PATENT DOCUMENTS

| | | | | |
|---|---|---|---|---|
| 6,134,806 A | * | 10/2000 | Dhaemers | ............... F26B 9/006 |
| | | | | 34/235 |
| 2015/0283339 A1 | * | 10/2015 | Mahadevan | ........ A61M 15/002 |
| | | | | 128/203.14 |

FOREIGN PATENT DOCUMENTS

WO WO-2013012696 A1 * 1/2013 ............... A61L 2/10

* cited by examiner

*Primary Examiner* — Kevin Joyner
(74) *Attorney, Agent, or Firm* — Grossman, Tucker, Perreault & Pfleger, PLLC

(57) ABSTRACT

The present invention is generally related to an apparatus and method for sanitizing a continuous positive airway pressure (CPAP) device, in particular the invention relates to a system, method and device that attach to a CPAP device and sanitizes all of the parts of the CPAP device, including the inner areas of the hose, reservoir and face mask most prone for bacteria buildup. The device has an ozone operating system and one or more ozone distribution lines that distributes ozone to a CPAP device and a non-permeable bag for sanitizing a CPAP mask.

10 Claims, 4 Drawing Sheets

Related U.S. Application Data application No. PCT/US2015/029418 on May 6, 2015, now Pat. No. 9,907,872.

(60) Provisional application No. 61/989,104, filed on May 6, 2014.

(51) Int. Cl.
*A61M 16/08* (2006.01)
*A61M 16/16* (2006.01)

DEVICES, SYSTEMS AND METHODS FOR OZONE SANITIZATION OF CONTINUOUS POSITIVE AIRWAY PRESSURE DEVICES

FIELD OF THE INVENTION

The present invention is generally related to a device and method for sanitizing all of the parts of a continuous positive airway pressure device with ozone, with an easy to use device that can distribute ozone through a continuous positive airway pressure (CPAP) device in between user cycles using an easily portable device. In particular the invention relates to a device and method for sanitizing the inside of the component parts of a continuous positive airway pressure device, in a device that attaches to any CPAP device as an attachment, as a first automated sanitization device and method to sanitize CPAP devices. The devices and methods of the present invention readily sanitize a CPAP device in between uses with a small battery operated ozone generating device, a distribution channel and a specialized connector unit to connect the ozone generating device to a CPAP device as a permanent attachment, and a non-permeable attachment bag for sanitizing a CPAP face mask.

BACKGROUND OF THE INVENTION

Sleep apnea is a common sleep disorder characterized by abnormal breathing during sleep. Pauses in breathing for people with sleep apnea can last from a few seconds to minutes during sleep, often resulting in significant levels of sleep disturbance, which may result in daytime fatigue, impaired reaction time, vision problems, and impaired daytime cognition.

Sleep apnea is often treated with a continuous positive airway pressure (CPAP) device. CPAP devices prevent reduction of oxygen levels in the blood and sleep loss by delivering a stream of pressurized air through a hose to a nasal pillow or a full face mask surrounding a patient's nose. The CPAP devices work by applying a mild air pressure on a continuous basis to keep a patient's airways continuously open at a prescribed pressure for each patient, to maintain unobstructed breathing throughout a sleep period, with patient initiated breaths.

While CPAP treatment can be a highly effective treatment for sleep apnea, a major downside with CPAP treatment is non-compliance. Patients are often reluctant to continuously use CPAP devices, as cleaning maintenance of CPAP devices have proved to be tiring and difficult for users because of bacterial buildup, which requires continuous cleaning and prevention steps. When users are away from home or traveling, cleaning of CPAP devices is even more difficult and cleaning compliance is less regular for users who are frequently travelling, such as truck drivers, pilots and business people with a heavy travel schedule. Most manufacturers of CPAP devices recommend that users perform daily and weekly cleaning of their machines to prevent bacteria and mold buildup. In this instance, each part of the CPAP device needs to be cleaned individually, including the mask, the hoses and the humidification portion, which is difficult and time consuming for users on a daily or weekly basis particularly when a user is travelling. Other CPAP device cleaning methods include soaking the component parts of a CPAP device in a mixture of vinegar and water to disinfect the component parts. Because of the inherent nature for CPAP devices to collect bacteria and mold, a number of other products are available to consumers to make CPAP machines safer, including but not limited to:

Citrus II Cleaning Spray for masks and tubing, available at www.cpapxchange.com

Contour CPAP cleaning wipes

CPAP tube cleaning brushes, available at www.cpapxchange.com

CPAP Guardian, available at www.cpapguardian.com

Further, several patents and patent applications have been filed on CPAP devices, improvements and the like. The patents in the field of CPAP devices include U.S. Pat. Nos. 7,845,350, 7,676,276, 6,276,304, 7,527,603, 7,767,168, 6,280,633, 7,022,225, 4,787,980 and US application numbers: 20100111792, 20060130834, 20040251125, 20050186108.

While some of the existing products, patents and applications described above refer to CPAP systems, methods and devices, there is no system, method or apparatus shown that covers the need to have an ozone system to sanitize, disinfect and clean a CPAP device and the inside of its component parts in a battery operated compact travel device that is easy to use while travelling, for ease of use and improved compliance of users, as described in accordance with the present invention.

Other systems, methods, apparatus features, and advantages of the present invention will be or become apparent to one with skill in the art upon examination of the following drawings and detailed description. It is intended that all such additional systems, methods, apparatus features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
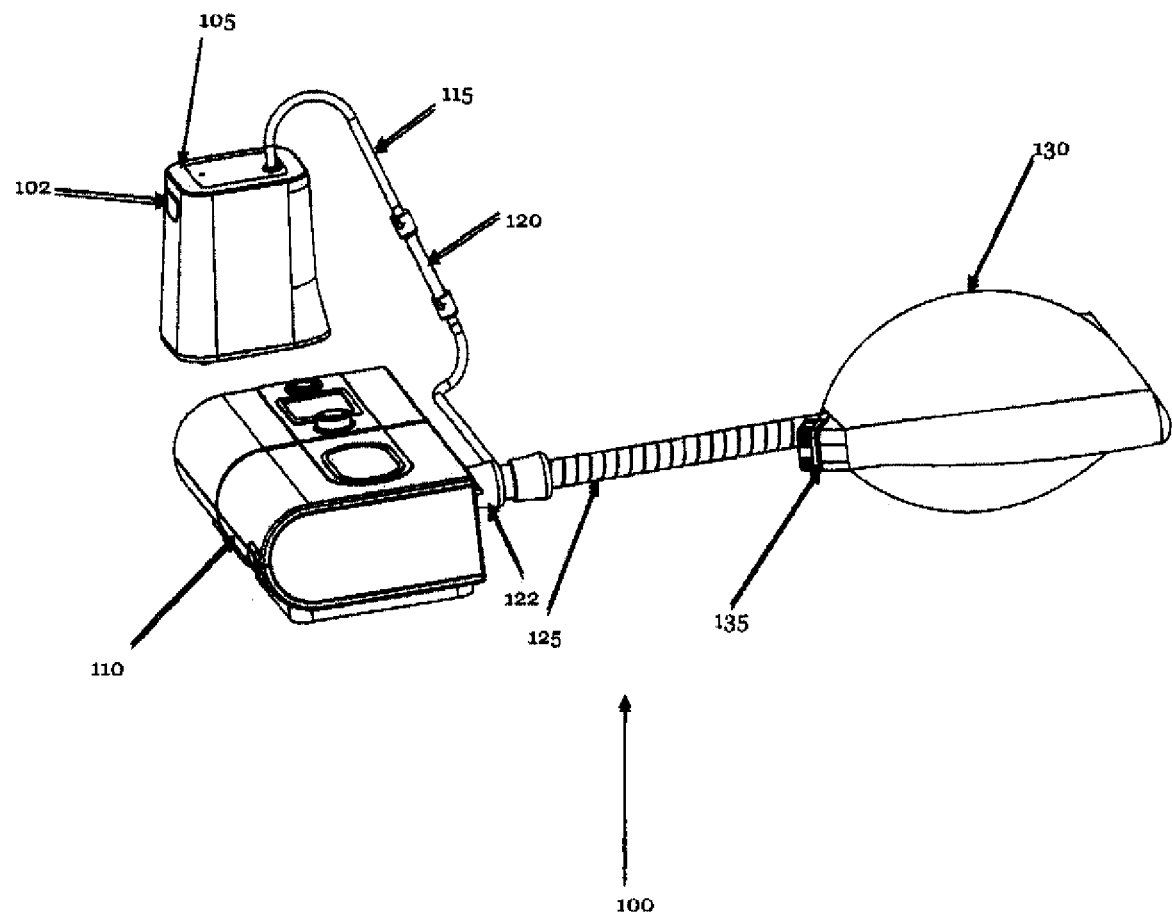
FIG. 1 is a perspective view of an apparatus for sanitizing a continuous positive airway pressure device, in accordance with the present invention.

FIG. 1 is a perspective view of a device 100 for sanitizing a CPAP device 110 in accordance with an embodiment of the present invention. In accordance with this embodiment, an ozone operating system is embedded in a portable device 105. A distribution line 115 is shown connecting the portable device 105 with an ozone operating system to a CPAP device 110, to distribute ozone generated in the ozone operating system to the inside of a CPAP device 110. In accordance with this embodiment, a CPAP connector unit 122 is attached to one end of a CPAP hose 125, wherein the distribution line traverses the CPAP connector unit 122 while maintaining the hose in an open position to receive air and ozone gas from said CPAP device 110. The other end of the CPAP device 110, in accordance with the present embodiment, is attached to a non-permeable bag 130 that is not permeable to ozone gas, for sanitizing a CPAP facemask when placed in the bag. Having the CPAP face mask separately enclosed in a compartment is an important feature of the present embodiment for complete sanitization of the CPAP device 110 and its component parts. Because the facemask touches the outer skin of a user, both the inside and the outside of the face mask must be sanitized. In this embodiment the non-permeable bag is made of several layers of fabric including but not limited to 1) an acrylic inner layer, 2) a high density polyethylene 3 layer barrier liner, and 3) an acrylic fabric shell, which combined prevents corrosion of the materials during the sanitization process and prevents leakage of ozone from the non-permeable bag into the ambient environment. In addition, in order to seal the non-permeable bag 130 in accordance with the present embodiment, Kevlar thread, nylon strings and cord locks are used to provide a tight drawstring seal to the non-permeable bag 130.

In accordance with the present embodiment, when a user is using a device, pressurized or humidified air will traverse from the CPAP device 110, through the CPAP connector unit 122, into the hose 125, and then to a face mask which a user where's around the user's mask, for providing regulated and pressurized air to a user while sleeping, to prevent pauses in breathing associated with sleep apnea. When a user is not using their CPAP device 110, the ozone operating system in the portable device 105 may distribute ozone to sanitize the CPAP device and its component parts either automatically, according to a timer, or with the start of a button. The ozone operating system in the portable device 105 will then distribute ozone gas through the distribution line 115 to the CPAP connector unit 122, into the hose 125 and to the non-permeable bag 130 for sanitizing a face mask in the non-permeable bag. Ozone gas is a powerful sanitizing gas, with significantly more sanitizing power in its gaseous form, as opposed to when ozone has been combined with water. In the present invention, the CPAP device 110 may have water in the water reservoir, when the ozone gas is distributed into the CPAP device 110. In accordance with this embodiment, the ozone gas may be used to sterilize the water in the CPAP device, and then release from the water as gaseous ozone quickly because the CPAP water is kept in a warm condition. The ozone gas will then traverse through the hose of the CPAP device, thereby sanitizing the inside of the hose, and then the ozone gas will traverse to the non-permeable bag for sanitizing the face mask.

About 20-30 minutes from the start of the ozone sanitizing process described, the ozone will start to naturally breakdown into oxygen $O_2$, which can then be safely released into the ambient environment. As an additional safety precaution to make sure all ozone is released, a filter cartridge 135 is provided on the side of the non-permeable bag 130, which is an oxidizing catalyst, such as an $MGO_2$ filter, to collect, breakdown and release remaining ozone as oxygen $O_2$. Further in accordance with this embodiment, a built-in timer and start button 102 on the portable device 105 allows a user to simply press a start button and the ozone sanitization process in accordance with this embodiment of the present invention is initiated. In accordance with the apparatus shown in FIG. 1, the ozone operating system will produce ozone when a user presses a start button 102 on the potable device 105.

To generate ozone, in accordance with an embodiment of the present invention, any available ozonator or like apparatus for creating ozone gas may be used. Ozonators create ozone from oxygen molecules, often by applying ultraviolet light to the oxygen or by using a corona discharge. Ozone gas is made of oxygen molecules that have been ionized by radiation to form groups of three oxygen atoms, $O_3$. The ozone gas is powerful and effective for removal of odors, impurities and dangerous pathogens, working by exchanging electron charge with particles that ozone comes into contact with to form oxygen, $O_2$, from the unstable ozone $O_3$, a process particularly useful for purifying air and water and for killing bacteria and microorganisms. Typically, ozone, $O_3$, will start to convert back to oxygen, $O_2$, within 30 minutes of the start of a cycle in accordance with the present invention.

Figure 2:
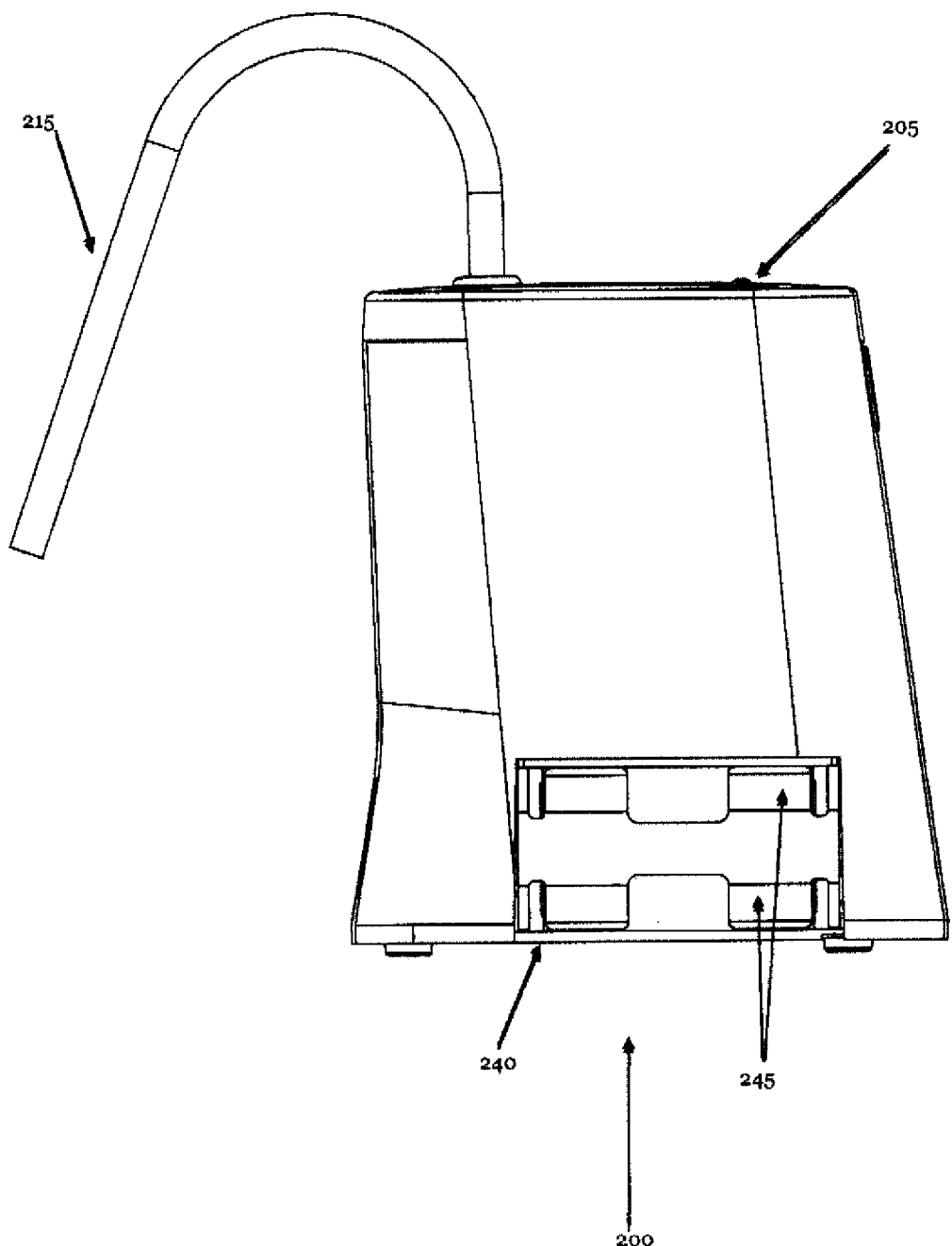
FIG. 2 is a side view of an apparatus for sanitizing a continuous positive airway pressure device, in accordance with the present invention.

FIG. 2 is a side view of the ozone apparatus in accordance with an embodiment of the present invention. In accordance with this embodiment, the convenience of a portable, battery operated ozone apparatus 200 is apparent. In this embodiment battery compartment 240 is shown for containing a battery for powering the ozone apparatus 200. In accordance with this embodiment, the batteries 245 may be any standard sized battery, such as double AA, or triple AAA batteries, rechargeable batteries, or a specialized battery developed for the ozone apparatus 200, which may be easily recharged by a user. In accordance with the embodiment shown, eight double AA batteries are used to power the portable device 205. In this embodiment, the distribution line 215 is also shown for attaching to a CPAP device in accordance with the present invention. The apparatus 200 in the present embodiment may also be used to sanitize a variety of devices, parts and other medical equipment, by attaching the distribution line 215 to another device, using the non-permeable bag for holding medical parts that require sanitization, along with other obvious products that would be benefitted from an easy and portable sanitizing device and system. In yet other embodiments of the present invention, a base attachment can replace the battery pack, allowing a user to plug in to an AC wall outlet or a 12 VDC automotive power supply.

Figure 3:
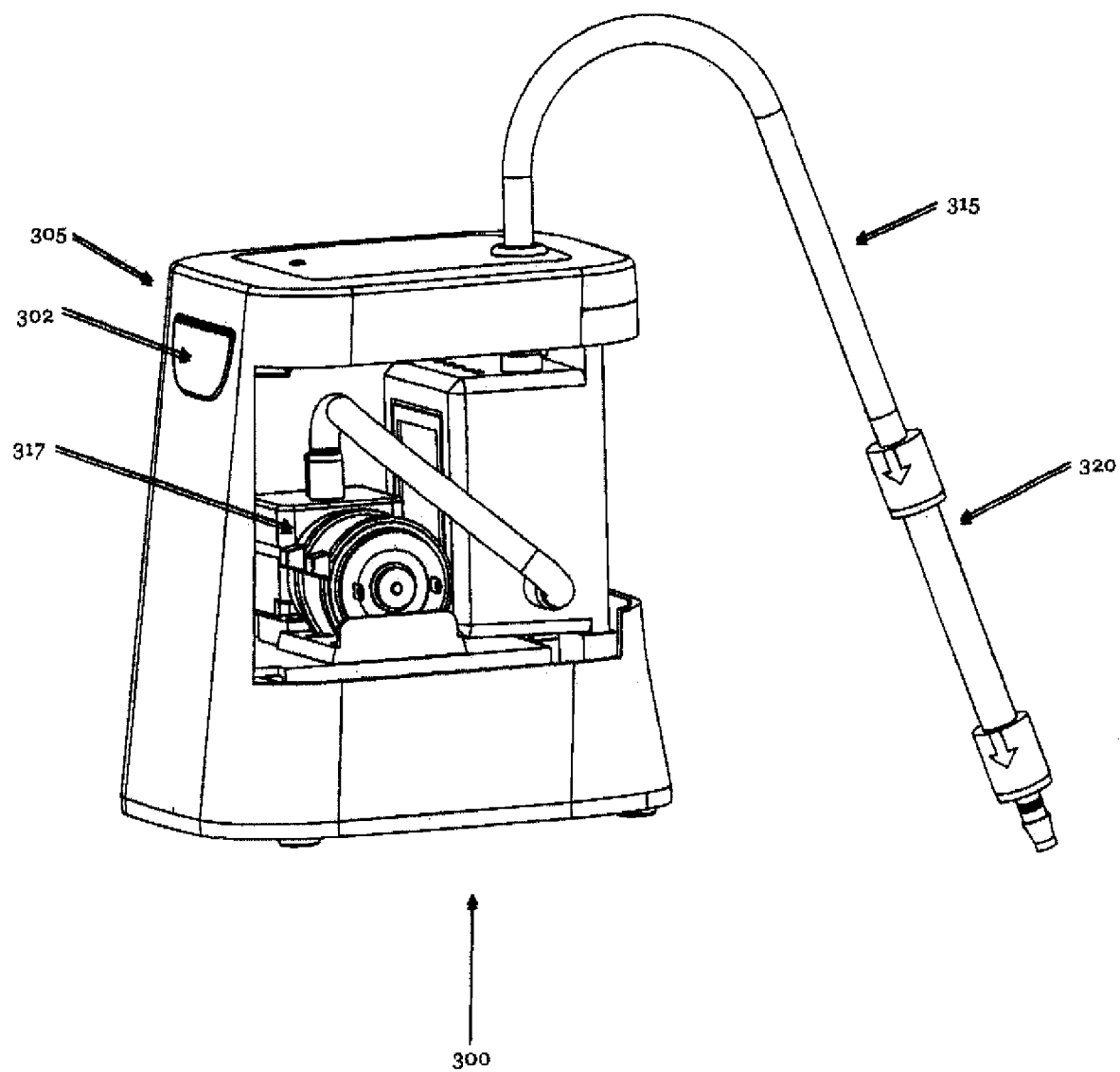
FIG. 3 is a cut out view of a portable device for sanitizing a continuous positive airway pressure device, in accordance with the present invention.

FIG. 3 shows a perspective cut-out view of an apparatus 300 in accordance with another embodiment of the present invention. In accordance with this embodiment, the ozone operating system 317 is shown in this cut out view of the portable device 305 showing the inside of the portable device 305. In accordance with this embodiment, the ozone operating system 317 will produce ozone, which will traverse through the hose 315 for sanitizing a CPAP device. Check valve 320 is further shown in this embodiment for preventing backflow of water from the CPAP water reservoir into the hose 315. The start button 302 is also shown for initiating the sanitization process, for ease of review and for the user's safety while the apparatus 300 is producing and transferring ozone throughout the apparatus 300.

Figure 4:
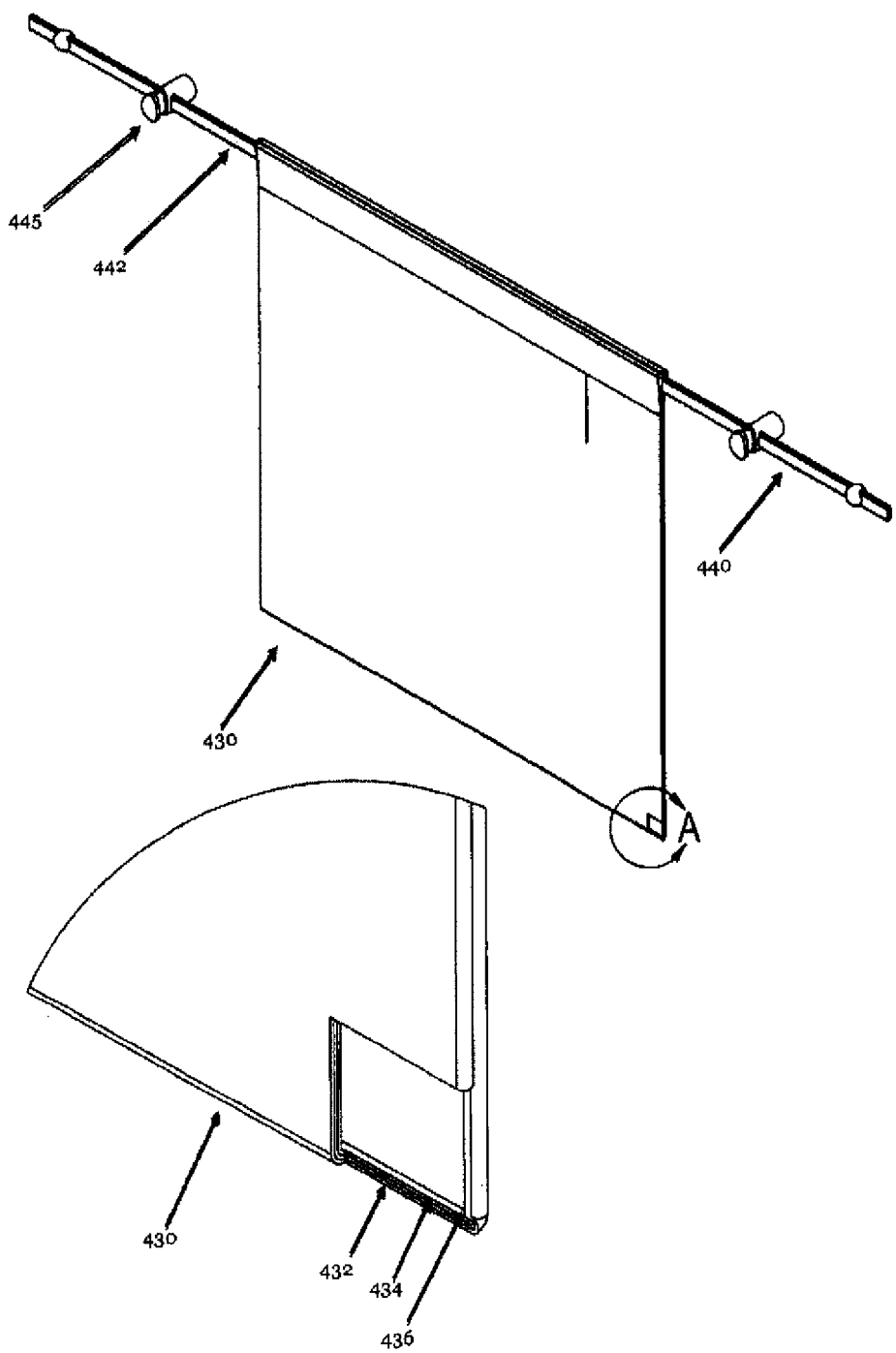
FIG. 4 is a perspective view of a non-permeable bag and a partial cut out view of a non-permeable bag in accordance with an embodiment of the present invention.

FIG. 4 shows a perspective of a non-permeable bag 430 and a cut out portion of the non-permeable bag 430, showing multiple layers of fabric for forming the non-permeable characteristic of the bag. In accordance with this embodiment of the present invention, non-permeable means the fabric is not permeable to ozone, which is an important safety criteria to keep ozone from the ambient air during the sanitization process. In accordance with this embodiment, an acrylic inner layer is provided, 432, along with a high density polyethylene barrier layer 434 and an acrylic fabric shell layer, 436 in the walls of the non-permeable bag 430. In addition, a sealing mechanism is provided with the non-permeable bag 430, shown in FIG. 4, in which the at least two drawstrings 442 are used to close the non-permeable bag 430. In accordance with this embodiment, pulling of the drawstrings 442 will tighten the top of the non-permeable bag 430 around the facemask that has been placed by a user into the non-permeable bag 430. Spring loaded adjusters 445 are provided to keep the non-permeable bag 430 in a tightly sealed position when the non-permeable bag 430 is closed for a sanitizing process, in accordance with the embodiment shown.

In accordance with one or more embodiments described herein, a device for sanitizing a continuous positive airway pressure device, is generally described, with an ozone operating system, a connector unit, wherein the connector unit, connects one end of a CPAP hose to a continuous positive airway pressure device and distributes ozone into a CPAP device, one or more ozone distribution lines, wherein the one or more ozone distribution lines traverses the connector unit into the CPAP device such that the hose remains open for receiving pressurized air and ozone gas from the CPAP device; and, a non-permeable bag connected to the other end of said hose, wherein a CPAP facemask may be sanitized in the non-permeable bag with ozone. The non-permeable bag in accordance with one or more embodiments may further include a sealing mechanism to prevent ozone leaks from the non-permeable bag and a filter cartridge for releasing ozone at safe levels into the ambient air, once a sanitizing cycle is complete.

In accordance with one or more embodiments of the present invention, water in a water reservoir in the CPAP device. In accordance with this embodiment the distribution line will traverse the CPAP connector unit with a free end immersed in the water in a water reservoir in the CPAP device. In accordance with this embodiment, ozone is released into the water, and will effectively sanitize the water in the water reservoir. While ozone is effective to sanitize the water, ozone immersed in the water will not effectively sanitize the remainder of the CPAP device, in particular, the water reservoir where there is no water, the hose and the facemask, all of which are prone to bacterial growth which pose risk of infection to a user, since the sanitizing power of ozone is significantly diminished when the ozone is immersed in water. However, in accordance with the present embodiment, ozone is released from the water in the water reservoir back into ozone gas at a quick rate because the ozone in the CPAP reservoir is typically at a warm temperature, which releases ozone back to it's gaseous form quickly, $O_3$. Ozone will travel from the reservoir through the connector unit, which is designed to keep air and ozone access to the hose, and into the hose. The ozone will then travel through the hose into the face mask, which is in a non-permeable bag, allowing the hose which touches a patients skin on a regular basis to be sanitized on both the inside and outside. One or more of the present embodiments may be performed by a user by pressing a button, or by setting a daily or weekly routine and automated sanitizing and maintenance schedule. In accordance with this embodiment, water remaining in the reservoir between uses can be easily sanitized in addition to the CPAP device and each of it's component parts—generally comprising a reservoir, a hose and a face mask, though different CPAP devices may have additional parts that can further be sanitized in accordance with the embodiments of the present invention. The devices in accordance with one or more embodiments of the present invention may further include a check-valve in the ozone distribution line, to prevent the back flow of water from a reservoir, into the ozone distribution line.

The device in accordance with the embodiments of the present invention can remain as a permanent attachment to any CPAP machine. Because the CPAP devices and hose attachments differ between models and vendors of CPAP devices, the present invention accommodates by making connector units that are devised to fit between specific CPAP devices and the related hose or similar mechanism, so that a device with an ozone operating system, a distribution line, a specialized connector unit to connect the hose to a particular model or brand of CPAP device and a non-permeable bag can be used and manufactured to fit as a permanent sanitizing attachment to any CPAP device on the market, for ease of use by a user. By providing the devices, systems and methods of the present invention as a sanitizing attachment to a CPAP device, provides for a significant step in ease of sanitizing CPAP devices, compared to conventional methods requiring a user to break apart the CPAP devices and soaking the devices in water with soup.

In addition to the apparatus described and shown in the embodiments of the present invention, methods for sanitizing a CPAP apparatus and its respective parts are further disclosed. In accordance with one or more of the methods described of sanitizing a CPAP device, the following steps are included but not limited to: A method for sanitizing a continuous positive airway pressure device, the method comprising the steps of: providing a device with an ozone operating system, placing a connector unit between the CPAP device and a CPAP hose, sanitizing the entire device readily, with ozone as a sanitizing agent, providing one or more ozone distribution lines, wherein the one or more distribution lines traverses the connector unit and distributes ozone to a CPAP device while maintaining the hose in an open position to receive pressurized air and ozone gas from the CPAP device, and connecting the other end of the CPAP device hose to a non-permeable bag for sanitizing a face mask in the non-permeable bag, safely and effectively. The methods of one or more embodiment may further include providing batteries to operate a device with an ozone operating system, and providing a check valve assembly to prevent leaks from water in a water reservoir into the ozone distribution line.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A system for sanitizing components of a continuous positive airway pressure (CPAP) device, comprising:
   an ozone operating system, wherein the ozone operating system is fluidly coupled to a first end of a hose of a CPAP device;
   a bag comprising an inner layer, an outer layer, and a barrier layer between the inner and outer layers, wherein the bag is impermeable to ozone gas and wherein a second end of the hose is coupled to a mask within the bag; and
   a sealing mechanism to seal an opening in the bag, wherein said sealing mechanism is movable between an unsealed configuration and a sealed configuration.

2. The system of claim 1, further comprising a filter cartridge coupled to or disposed in said bag.

3. The system of claim 1, wherein said filter cartridge is provided on a side of the bag.

4. The system of claim 1, further comprising a portable device comprising said ozone operating system.

5. The system of claim 4, wherein said ozone operating system is battery powered disposed within the portable device.

6. The system of claim 1, further comprising a connector unit, the connector unit configured to form at least a portion of a fluid connection between the ozone operating system the first end of the hose.

7. The system of claim 1, wherein the second end of the hose is attached to the bag.

8. The system of claim 1, further comprising an exhaust filter for converting ozone to oxygen, the exhaust filter located downstream of the ozone generator.

9. The system of claim 1, wherein a reservoir is downstream of the ozone generator and upstream from the first end of the hose.

10. The system of claim 1, further comprising a check valve configured to prevent water from flowing from the water reservoir to the ozone operating system.

\* \* \* \* \*